(12) United States Patent
de Greef (10) Patent No.: US 6,553,814 B2
(45) Date of Patent: Apr. 29, 2003

(54) METHOD AND DEVICE FOR DETERMINING THE HARDNESS/ELASTICITY AND/OR OTHER PROPERTIES OF VEGETABLES OR FRUIT

(75) Inventor: Jacob Hendrik de Greef, Waardenburg (NL)

(73) Assignee: De Greef's Wagen-carrosserle-en Machinebouw B.V. (NL)

( * ) Notice: Subject to any disclaimer, the term of this patent is extended or adjusted under 35 U.S.C. 154(b) by 0 days.

(21) Appl. No.: 09/727,298

(22) Filed: Nov. 29, 2000

(65) Prior Publication Data

US 2002/0014112 A1 Feb. 7, 2002

(30) Foreign Application Priority Data

| Dec. 1, 1999 | (NL) | ................................................. | 1013720 |
| Aug. 16, 2000 | (NL) | ................................................. | 1015949 |
| Sep. 14, 2000 | (NL) | ................................................. | 1016186 |
| Oct. 20, 2000 | (NL) | ................................................. | 1016453 |

(51) Int. Cl.⁷ ............................................. G01N 33/02
(52) U.S. Cl. ........................................................ 73/81
(58) Field of Search .................... 73/78, 79, 81–83; 209/599–601

(56) References Cited

U.S. PATENT DOCUMENTS

| 4,061,020 A | 12/1977 | Fridley et al. ................. 73/81 |
| 4,974,443 A | * 12/1990 | Heitmann ....................... 73/81 |
| 5,315,879 A | 5/1994 | Crochon et al. ............... 73/818 |
| 5,806,686 A | 9/1998 | Ecker .......................... 209/615 |
| 5,811,680 A | 9/1998 | Galili et al. .................. 73/579 |

FOREIGN PATENT DOCUMENTS

| FR | 2702048 | 2/1993 |
| WO | WO 98/40737 | 3/1998 |
| WO | WO 98/52037 | 5/1998 |

* cited by examiner

*Primary Examiner*—Robert Raevis
(74) *Attorney, Agent, or Firm*—Needle & Rosenberg, P.C.

(57) ABSTRACT

The present invention comprises a method for determining the hardness of a vegetable or fruit, wherein the vegetable or fruit is rotated, wherein an impactor element is carried close to the surface of a fruit or vegetable, wherein during rotation of the fruit an impactor element is brought into contact with the fruit or the vegetable a number of times, wherein the impact of the respective impactor element is measured in order to determine the hardness of the vegetable or fruit over at least a portion of the surface thereof.

The present invention also comprises a device for determining the hardness of a vegetable or fruit.

The present invention further provides a method for determining a property of a vegetable or fruit.

22 Claims, 13 Drawing Sheets

METHOD AND DEVICE FOR DETERMINING THE HARDNESS/ELASTICITY AND/OR OTHER PROPERTIES OF VEGETABLES OR FRUIT

Vegetables and fruit such as apples, pears, tomatoes, citrus fruits and the like are selected in current practice on the basis of a large number of parameters, such as size, weight, color and the like. Because of increasing demands of consumers, there is now a trend toward also sorting fruits and vegetables according to hardness.

It is the current practice at auctions for an inspector to determine the hardness of a fruit in usually destructive manner by means of penetration with an impactor through about 2 cm. This hardness can have different values at different locations on the fruit. In the classification and selection of fruits there is therefore a need to determine the hardness of a fruit on the surface in non-destructive manner, for instance by means of non-destructive impact (or hardness) measurements.

In the international patent application PCT/GB98/01300 an impactor in a bellows is carried above one fruit or vegetable at a time, whereafter the local hardness derived from the elasticity is determined from the impact measured with a piezo-electric element.

This known method and device is however not suitable for performing measurements on fruits being supplied on a conveyor at a high speed, since the bellows must be brought close to the fruit each time. The hardness (or elasticity) of the fruit is furthermore determined at only one position, which provides an unreliable indication of the general hardness (and/or ripeness) of that fruit.

The present invention provides a method for determining the hardness of a vegetable or fruit, wherein the vegetable or fruit is rotated, wherein an impactor element is carried close to the surface of a fruit or vegetable, wherein during rotation of the fruit an impactor element is brought into contact with the fruit or the vegetable a number of times, wherein the impact of the respective impactor element is measured in order to determine the hardness of the vegetable or fruit over at least a portion of the surface thereof.

The impactor element preferably co-displaces with the fruit above the conveyor in order to enable a large number of measurements over the surface thereof while the fruit is supplied by the supply conveyor.

In another preferred embodiment of the method and device according to the present invention, it is likewise conceivable for a number of impactor elements to be in successive stationary disposition while the fruits are transported rotatingly thereunder (or over) on a conveyor. It is of course of equal importance here that the impactor elements can properly follow the contours of successive fruits or vegetables of perhaps differing diameter, for which purpose it is important that the impactor elements are freely movable in vertical direction.

The present invention further provides a device for determining the hardness of a vegetable or fruit, comprising:
a supply conveyor for supplying the vegetables or fruits,
rotation means for causing the vegetables or fruits to rotate on the supply conveyor; and
one or more hardness measuring members for measuring the hardness of the vegetables or fruits during rotation thereof, wherein the hardness measuring members are arranged above the supply conveyor.

In a further preferred embodiment of the device according to the present invention the hardness measuring members are arranged pivotally relative to each other or movable in height independently of each other in order to perform reliable hardness measurements on successive vegetables or fruits of different size.

In a first preferred embodiment the impactor element is lifted using a solenoid and then released, whereafter the impact thereof is measured using a piezo-electric transducer; in other embodiments mechanical lifting of the weight on the impactor element can also take place, wherein the impact is likewise determined by means of a piezo-electric transducer or with other means.

In a further preferred embodiment the hardness or impact transducer is arranged adjacently to a wheel or disc which rolls along the surface of a fruit and which, irrespective of the diameter thereof, prevents damage to this fruit. In the embodiment wherein the transducer co-displaces with the fruit, the hardness can be determined at any desired location along the surface, which increases the flexibility of the number of measurements and the speed of the conveyor.

The method and device according to the present invention can also be applied for other measurement principles, such as to determine the spectrum of the light reflected by the surface of a vegetable or fruit, the spectrum of the light passing through the object, the roughness of the skin of a vegetable or fruit, the analysis of the gases given off by the object and the like.

The present invention therefore also provides a method for determining a property of a vegetable or fruit, wherein the vegetable or fruit is rotated, wherein during rotation of the fruit the transducer is brought a number of times into the vicinity of the fruit or the vegetable, wherein the property is measured, in order to determine the property of a vegetable or fruit over at least a portion of the surface thereof.

The present invention further provides a device for performing such a method.

In order to prevent an (elongate) fruit which is supplied on a brush roller being forced laterally out of the conveyor path due to contact with a wheel or transducer, in accordance with another aspect the present invention provides a brush roller with one or more, preferably two, rings of slip-resistant material such as rubber. In a further preferred embodiment a sensor element or contact element is arranged between two diabolo-shaped elements in order to position the fruits properly and to obtain a reliable and accurate measuring result.

Further advantages, features and details of the present invention will be elucidated on the basis of the following description with reference to the annexed drawings, in which.

In a sorting line 1 (FIG. 1) fruits $V_1$, $V_2$ and $V_3$, for instance of differing size, are supplied in the direction of arrow A on a conveyor 3 provided with diabolos 2. Using a belt, rope or chain 4 driven in the direction of arrow B, the diabolos are rotated in a direction according to arrow C, whereby the fruits rotate in the direction of arrow D. The rotation direction D of the fruits, which is in fact in the direction opposite to transporting direction A, is recommended since, as will become apparent herein below, the hardness of the fruits is determined by means of mechanical contact. The advantage of this transporting direction is that the fruit displaces little during the momentary mechanical contact, less damage to the fruits will occur and/or the influence of occurring lateral forces will be less in evidence.

The above stated advantage is particularly important in a stationary disposition (not further shown), wherein a number of contact elements is disposed successively above the conveyor with diabolos. In the embodiment shown in FIG. 1, wherein the contact elements co-displace, it is also possible to envisage the fruits being rotated forward.

Figure 1:
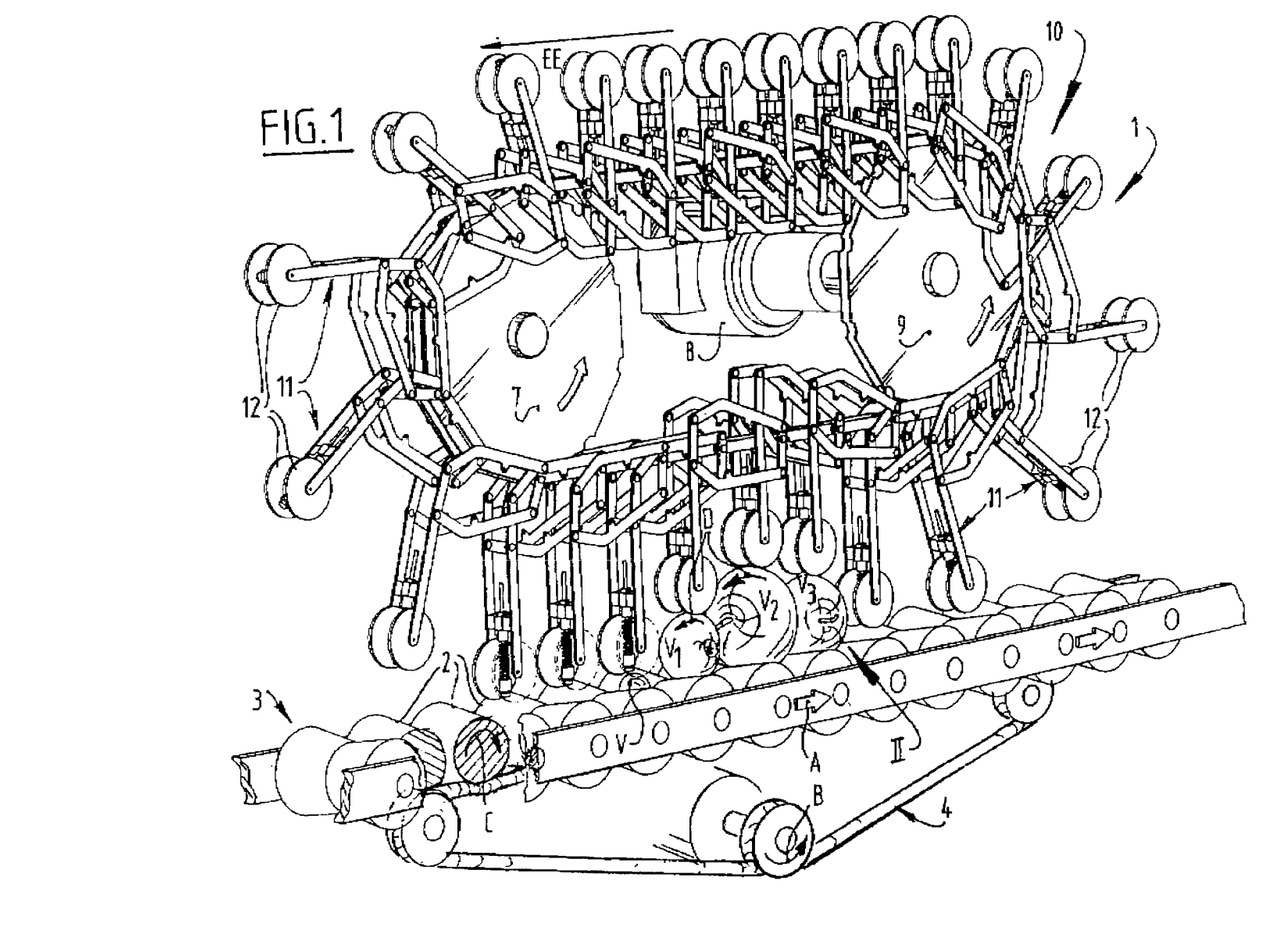
FIG. 1 shows a schematic view in perspective of a preferred embodiment of the device and method according to the present invention.

Arranged above conveyor 3 is a device 10 which comprises a number of contact elements 11 which are connected mutually pivotally and which are also provided on the ends with one or more discs or wheels 12 to allow such an element 11 to roll over a fruit $V_1$–$V_3$.

Reversing wheels 7 respectively 9 are driven using a schematically designated motor 8 in order to drive the contact elements 11 in the direction of arrow E at substantially the same speed as the transporting speed of conveyor 3, i.e. synchronously therewith. As shown particularly clearly in FIGS. 2 and 3, a pin 13 with a weight member 14 of predetermined value, for instance 10 grams, is situated in each case adjacently of a disc or wheel 12, wherein the weight is held in the rest position by a helical pressure spring 15. While a contact element 11 co-displaces with a determined fruit, a solenoid (not further shown) is released at predetermined times, whereby the weight 14 of predetermined mass on the impactor element drops against the surface of a fruit $V_1$, $V_2$ or $V_3$, whereby the degree of impact of that weight against the fruit, and thus the hardness of this fruit, can be determined by a piezo-electric transducer (not shown). An example of the co-action of a solenoid and piezo-electric element is described in for instance the above stated international patent application.

Because the contact elements co-displace with the conveyor and the fruit is simultaneously rotated, the hardness of the fruit can for instance be measured at 10 or more locations along the whole periphery of this fruit. In the case of small fruits a smaller number of measurements may already suffice.

Figure 2:
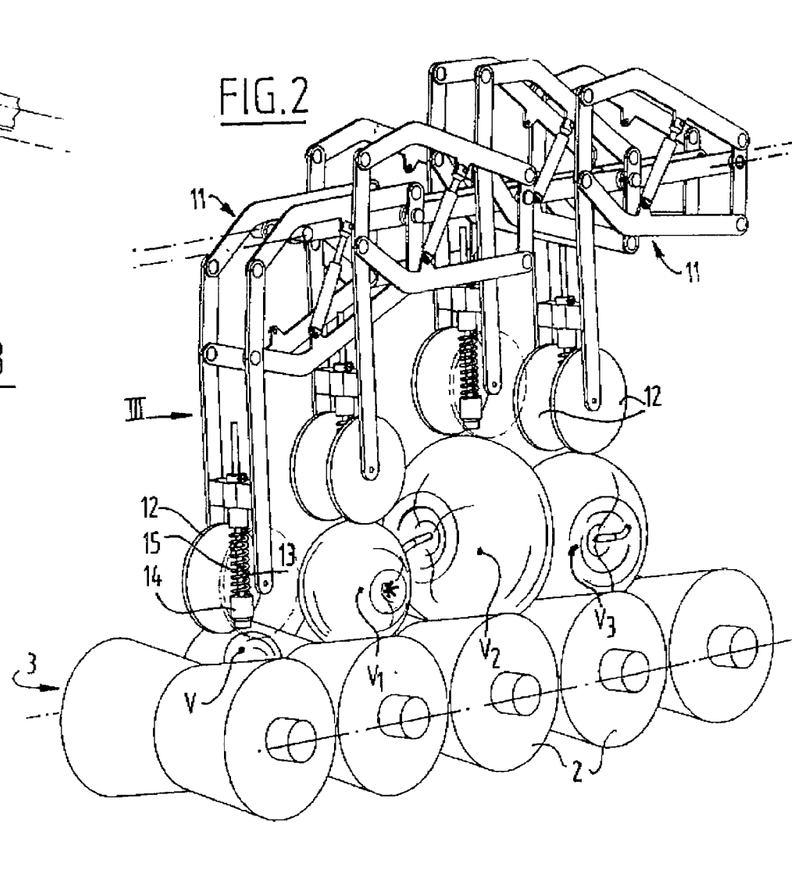
FIG. 2 shows a perspective view of detail II of FIG. 1.
Figure 3:
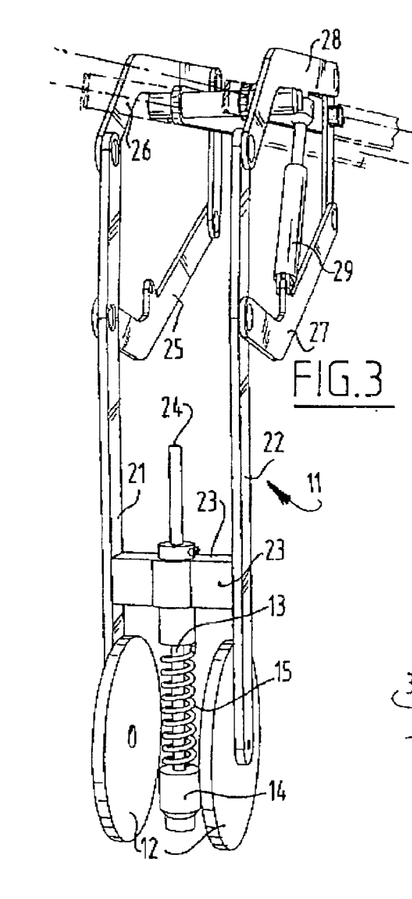
FIG. 3 is a front view in perspective of detail III of FIG. 2.

As shown particularly in FIG. 3, contact element 11 comprises two parallel arms 21, 22 with a connecting piece 23 arranged therebetween, wherein the solenoid and the piezo-electric element are arranged in a manner not shown. An electric lead 24 is also connected to this connecting piece 23. Pairs of curved arms 25, 26 respectively 27, 28, together forming a parallelogram, are further arranged pivotally on the mounting arm, while in the present embodiment a damper 29 (and/or a spring) is arranged between arms 27 and 28 in order to prevent damage to the fruits and/or optimize the response of the impactor. A subsequent contact element 11 can be mounted pivotally on contact element 11 as elucidated in FIGS. 1 and 2, so that the successive contact elements 11 can follow the fruits of differing diameter as well as possible.

In another, not shown, preferred embodiment the contact elements can likewise be mounted directly on a chain or toothed belt, wherein it must however be ensured that the contact elements can move sufficiently in vertical direction.

Figure 4A:
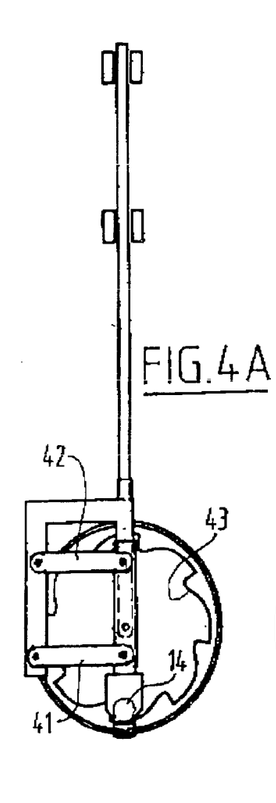
FIGS. 4A–4E are schematic side views of respective alternative embodiments of an impactor element to be applied in the embodiment according to FIG. 1.
Figure 4B:
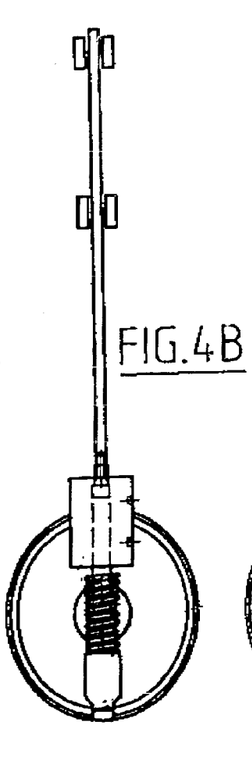
Figure 4C:
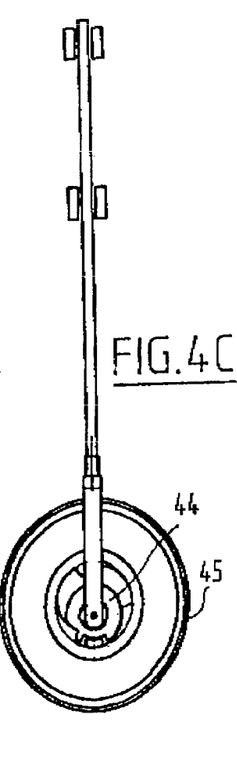

In the embodiments according to FIGS. 4A, 4C, 4D and 4E are shown schematic alternatives to the embodiment according to FIG. 4B. In FIG. 4A a weight 14 is moved mechanically upward in each case using parallel arms 41, 42 and a curve disc 43, while this mechanical transport is realized according to FIG. 4C using a curve 44 arranged internally on a disc 45, whereby the mass with the piezo-element is raised, whereafter it falls freely onto the inner side of the wheel. The pulse of the impact transmitted by the wheel to the measured product is measured by the piezo-element.

Figure 4D:
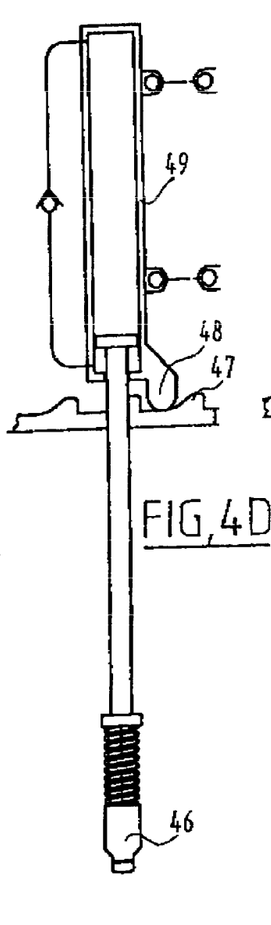
Figure 4E:
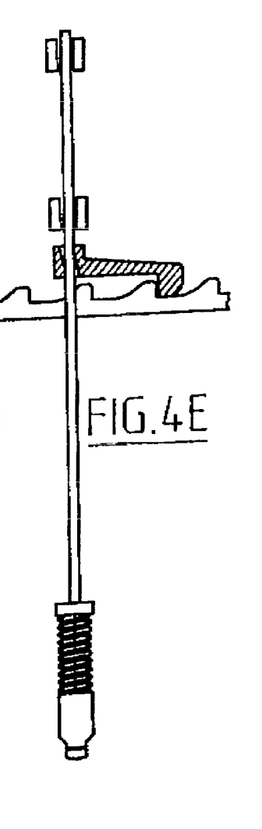

In the embodiment according to FIG. 4D a weight 46 is moved upward using a tooth path 47 and a cam 48, whereafter it can fall, while in order to avoid damage to the fruits a damper 49 can also be arranged. In the embodiment of FIG. 4E the damping can be obtained in a manner corresponding to the embodiment shown in FIGS. 1–3.

The preferred embodiments applied in FIGS. 4A–4E can likewise be applied in a stationary arrangement, i.e. wherein a number of such impactor elements is disposed mutually adjacently above the conveyor provided with diabolos, wherein the fruits are rotated and are measured in each case at a further location on the periphery thereof under a following impactor element.

Figure 5:
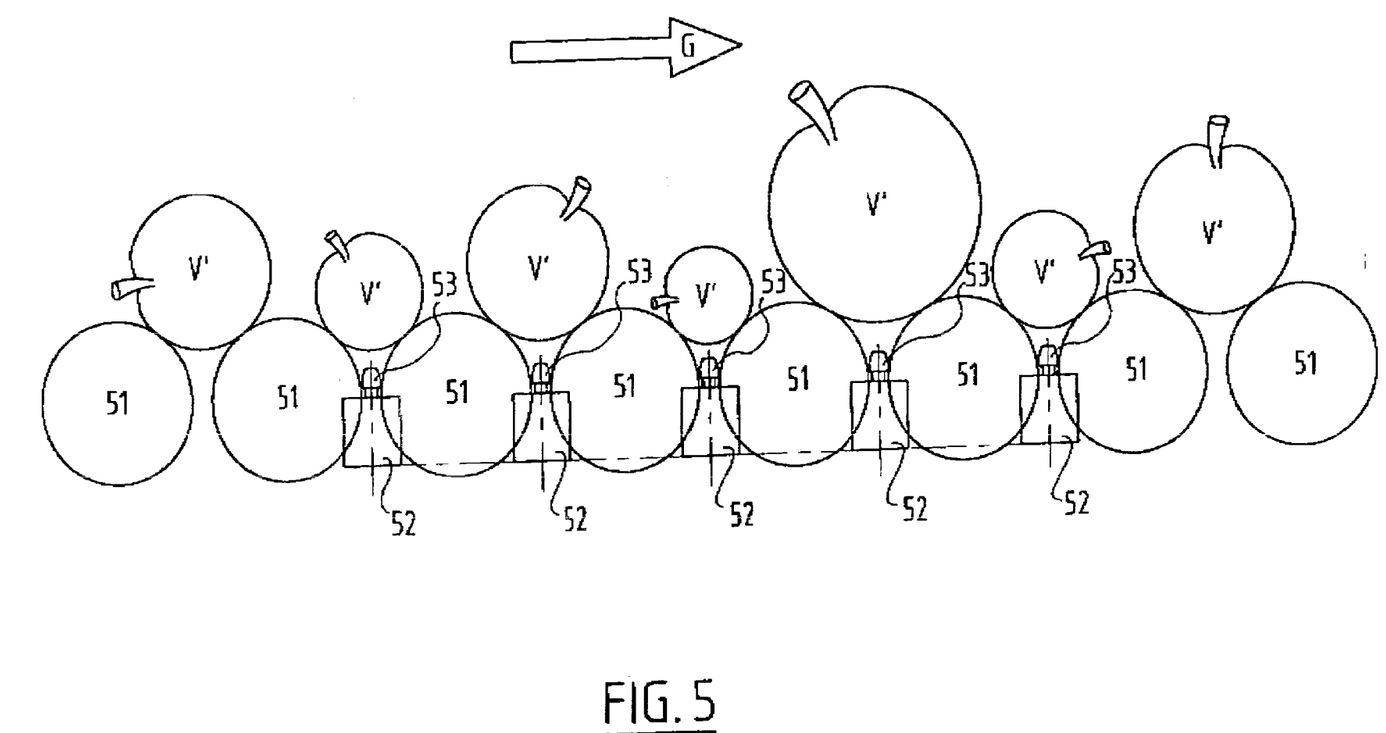
FIG. 5 shows a schematic side view of a further preferred embodiment of a device and method according to the present invention.

In the preferred embodiment shown in FIG. 5 the fruits V' of different diameter are transported in the direction of arrow G on a conveyor provided with diabolos 51, wherein impactor element 52 co-displaces between the diabolos 51 and during rotation of fruits V' a contact element 53 is jolted upward each time against fruits V' with a predetermined impulse, wherein in the manner described above the impact thereof is measured with for instance a piezo-electric element.

Figure 6:
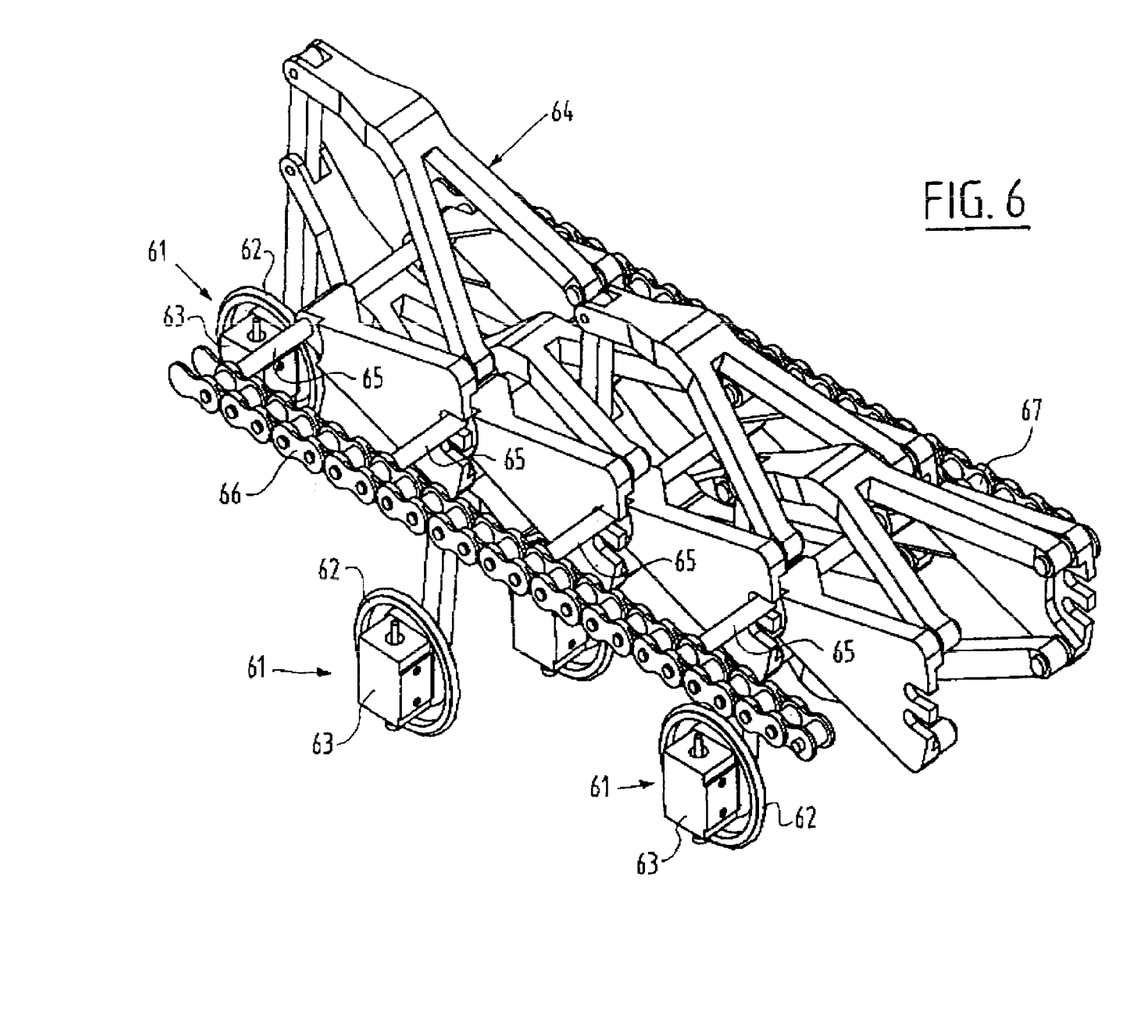
FIG. 6 shows a view of a further preferred embodiment of the device as according to FIGS. 1, 2 and 3.

In the embodiment shown in FIG. 6, which forms a further development of the embodiment shown in FIGS. 1, 2 and 3, each contact element 61 is provided with a single disc 62, within the periphery of which the impactor members 63 are arranged in each case. The construction 64, which enables elements 61 to move as freely as possible in vertical direction, is arranged on pins 65 which are advanced between chains 66 and 67 synchronously with the conveyor with diabolos, not shown in FIG. 6.

Figure 7:
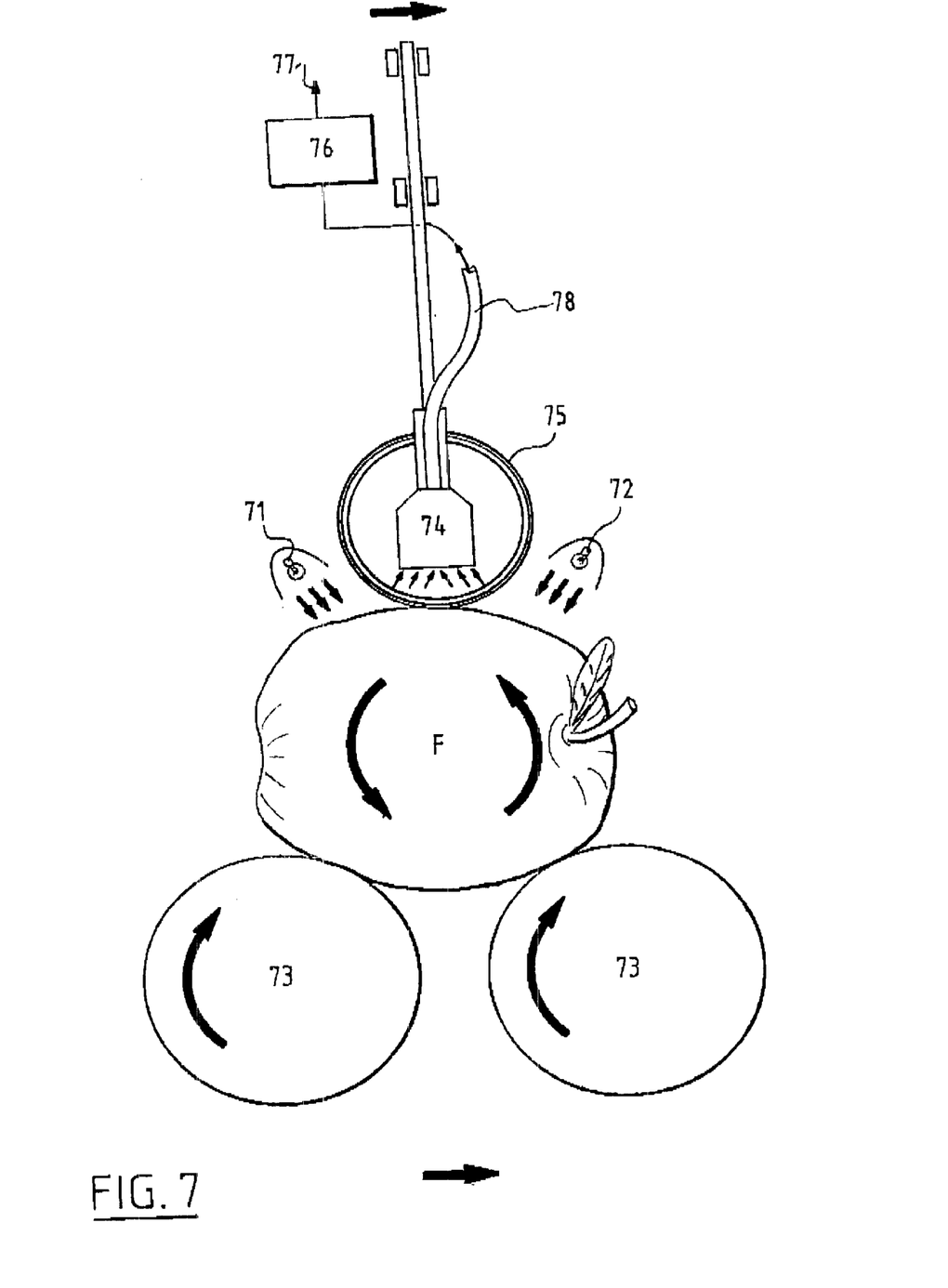
FIG. 7 shows a schematic view of a further preferred embodiment of a method and device according to the present invention.

In the embodiment according to FIG. 7 light is projected onto a fruit F rotated by transport rollers 73 using two light sources 71, 72, the reflection of which light is determined using an optical transducer 74 arranged adjacently of a wheel 75 which follows the surface of fruit F. Connected to transducer 74 is a glass fibre cable 78 which is connected on the other side to an analysis device 76 for analyzing the spectrum of the reflected light, on the basis of which an output signal 77 is generated by analysis device 76, which signal is a measure for the color of the fruit.

Figure 8:
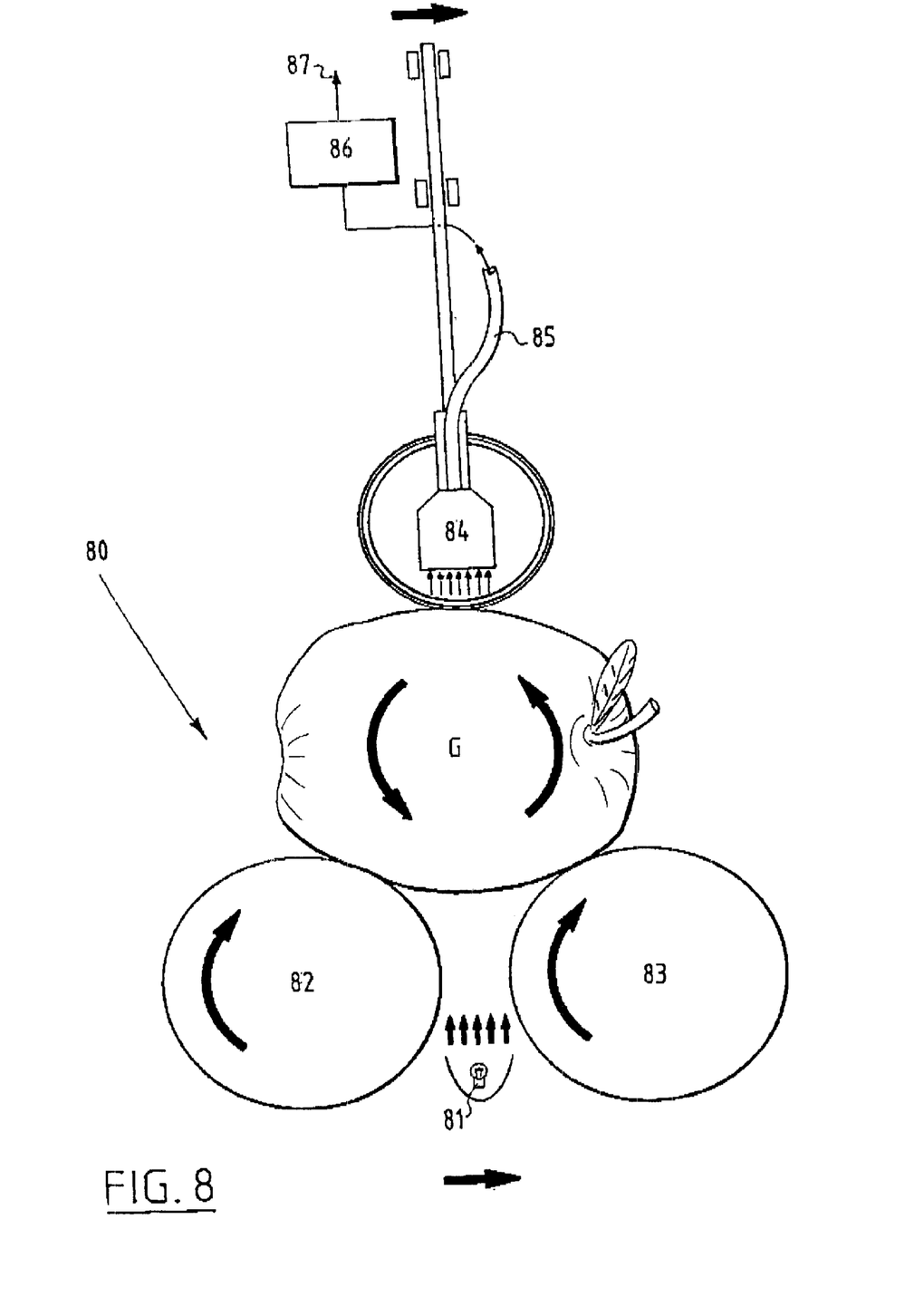
FIGS. 8, 9 and 10 are respective schematic views of further preferred embodiments of a method and device according to the present invention.

In the device 80 according to FIG. 8 light is projected between two transport rollers 82, 83 onto a fruit G by a light source 81, whereby fruit G is rotated, while the quantity of light let through by fruit G is measured by a transducer 84 which is connected to a spectral analyzer 86 via a glass fibre cable 85, the output signal 87 of which analyzer provides a measure for the quantity of light let through by the object.

Figure 9:
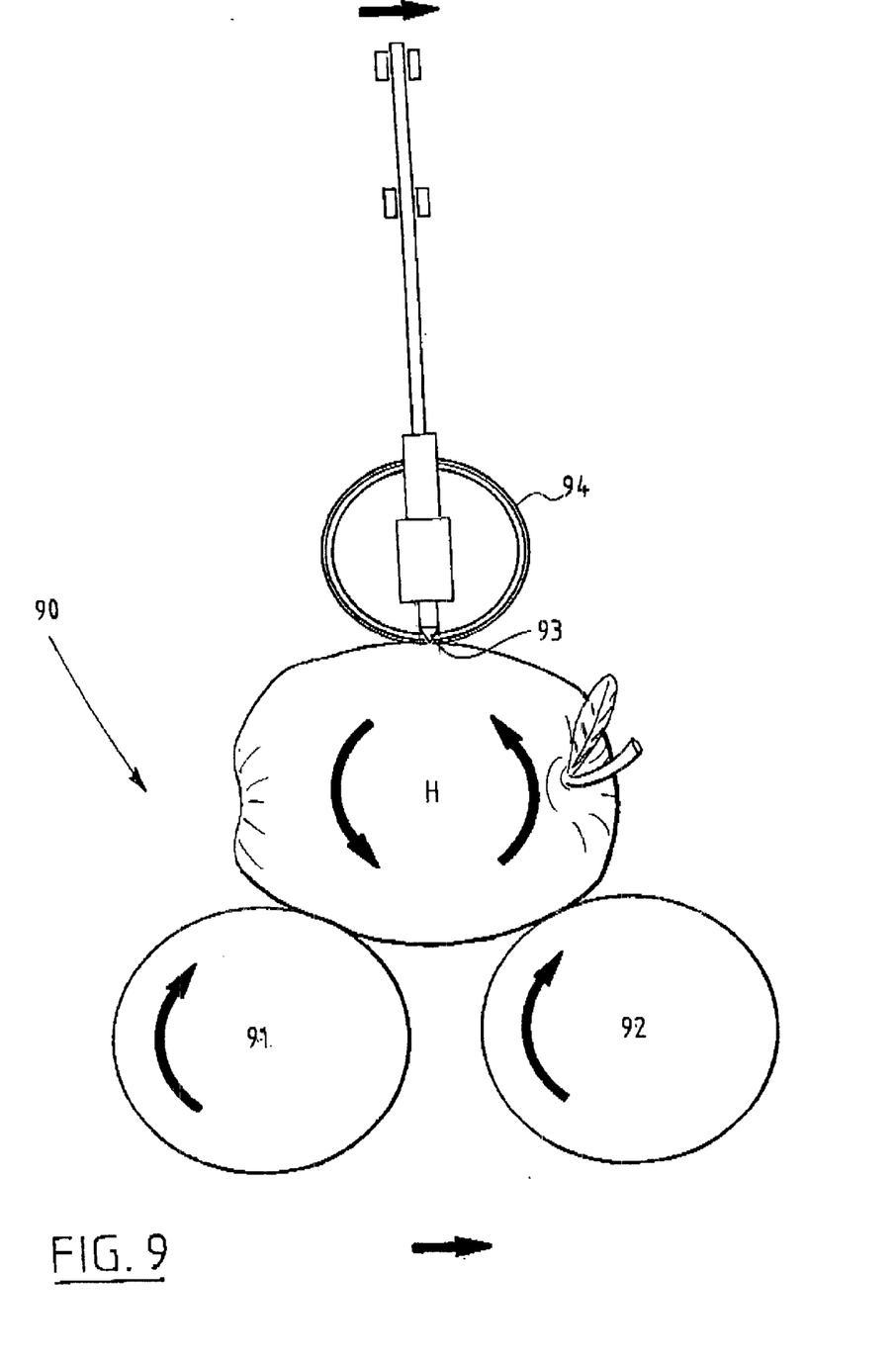

In the device 90 according to FIG. 9 a fruit H set into rotation by transport rollers 91 and 92 is scanned using a scanning member 93, which is arranged adjacently of a tracking wheel 94 in order to enable determining of the roughness of the surface of fruit H from the movements of scanning member 93.

Figure 10:
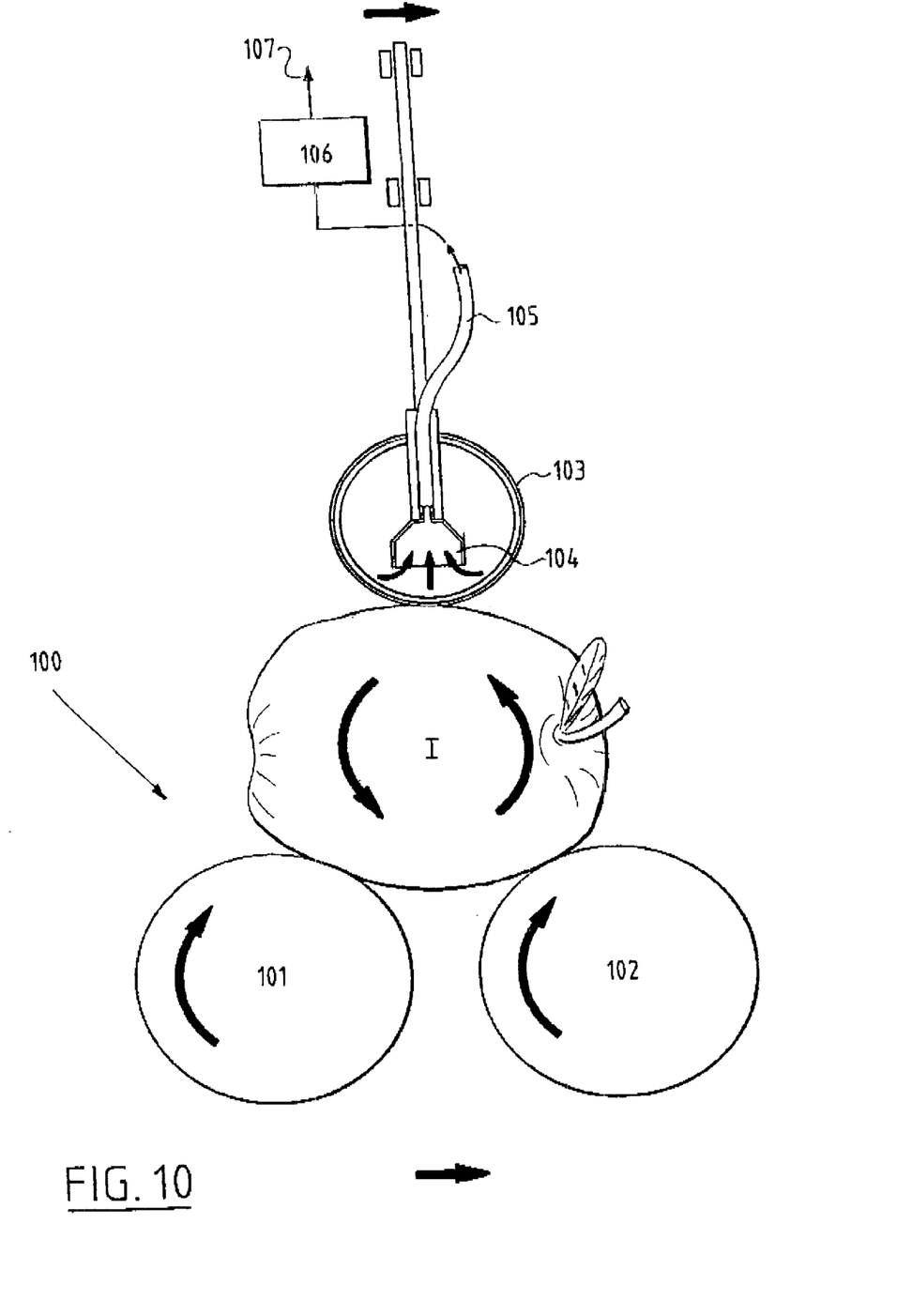

In the device 100 of FIG. 10, wherein a fruit I is rotated by transport rollers 101, 102, the gases given off by fruit I are taken up using a sniffer member 104 arranged adjacently of a tracking wheel 103 and guided further via a hose 105 to a gas analysis device 106 for the purpose of generating an electrical signal 107 which forms a measure for the quantity and/or composition of the gases given off by a fruit, and thus for instance for the ripeness thereof.

Figure 11:
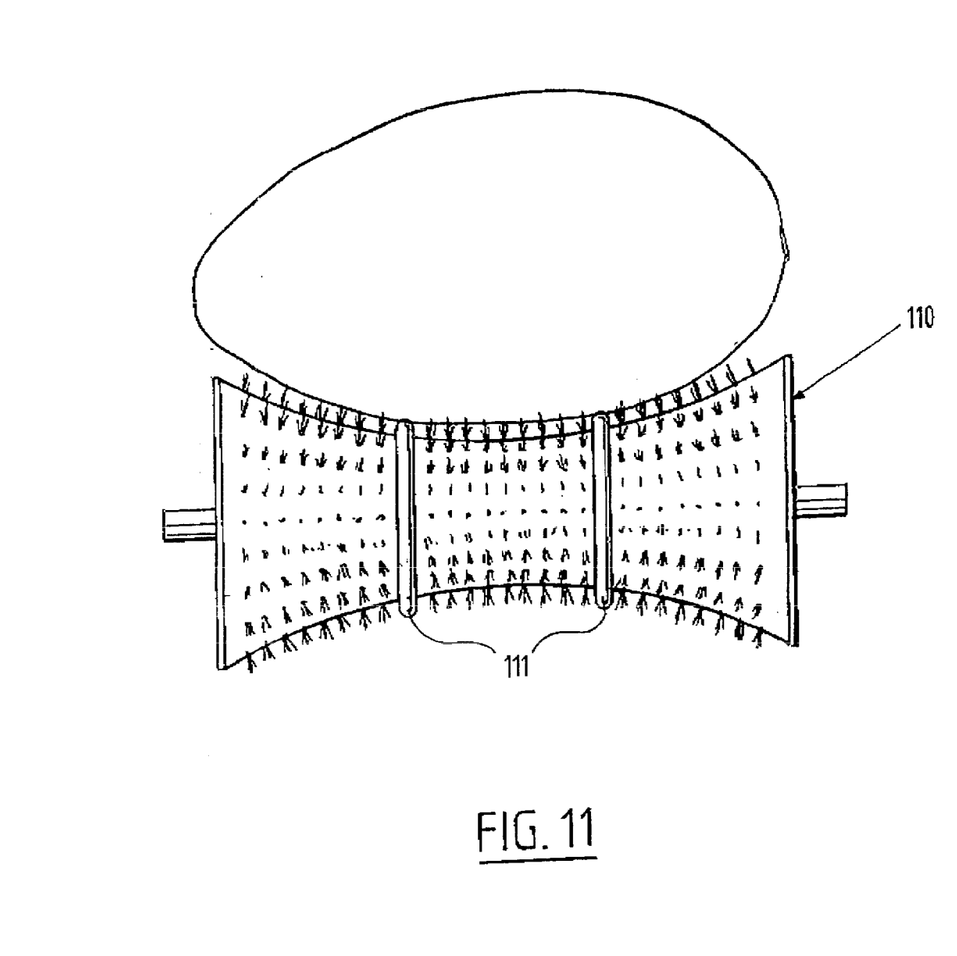
FIG. 11 is a view of a brush roller with two slip-resistant rings.

In the case of for instance elongate and vulnerable fruits, such as avocados and pears, which are usually supplied on brush rollers, the problem can occur of these fruits being urged sideward when there is contact with a wheel on the upper side. In order to prevent this the brush roller 110 of FIG. 11 is provided with two rubber rings 111, which ensure that a fruit undergoes sufficient lateral resistance.

Figure 12:
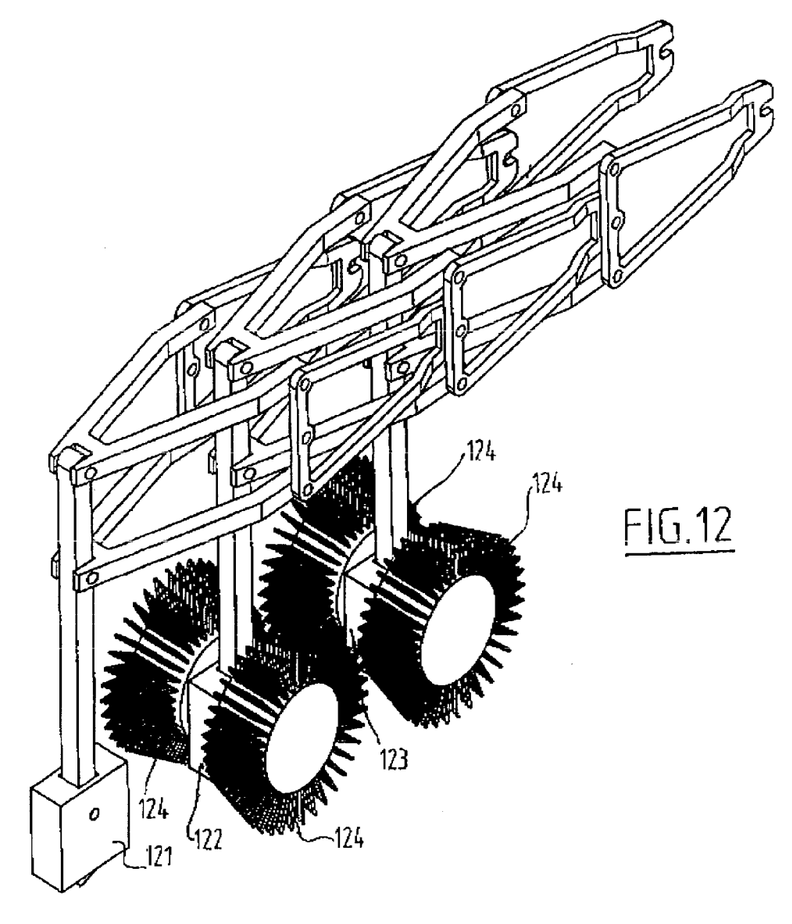
FIGS. 12 and 13 show further preferred embodiments of a part of a device according to the present invention.
Figure 13:
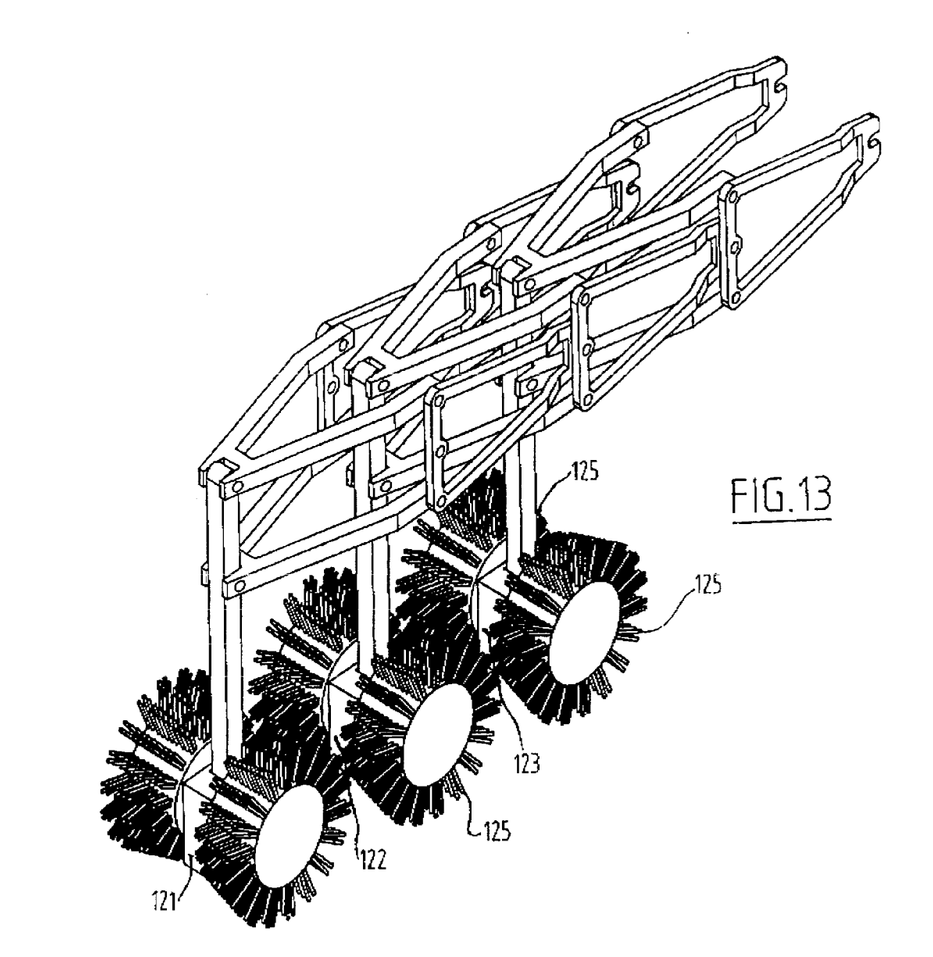

In a further preferred embodiment according to FIGS. 12 and 13 sensor elements 121, 122 and 123 are arranged between diabolo-shaped brushes 124 and 125, the density of which is different. The diabolo-shaped brushes enable good positioning of the fruits and an accurate and reliable measuring result can be obtained.

Dependent on the type of fruits, the rotating elements can however also be a diabolo-shaped smooth surface or even be provided with a flat surface of for instance plastic or rubber, which can also be locally rough.

Figure 14:
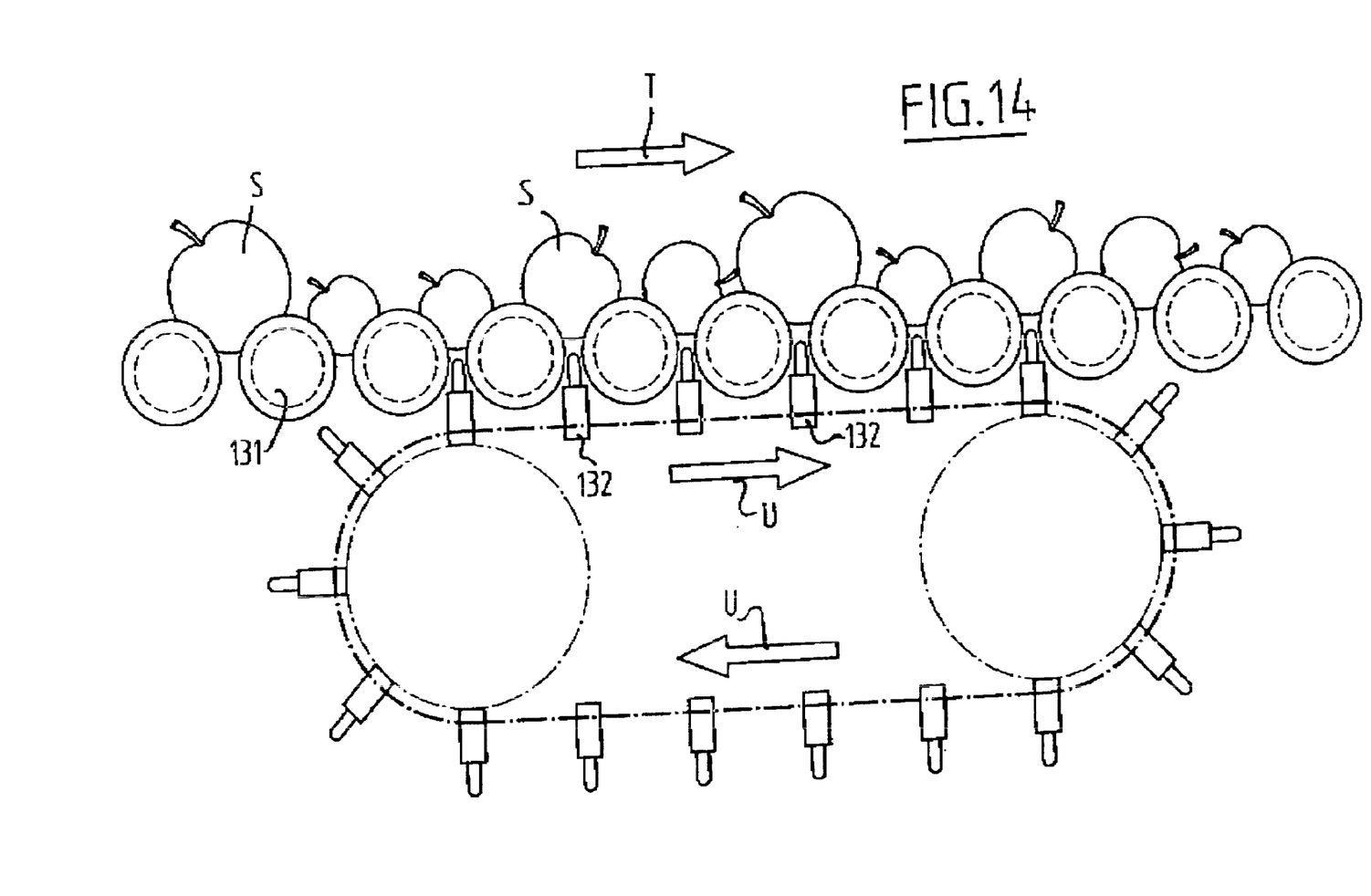
FIG. 14 is a schematic side view of another preferred embodiment of a device according to the present invention.

In the embodiment of FIG. 14 the apples are supplied on diabolos 131 in the direction of arrow T. Sensors 132 are arranged on an endless belt 133 in the direction of arrows U which is moved synchronously with diabolos 13 such that the sensors protrude in each case precisely therebetween. This embodiment is particularly advantageous with batches of fruits with very large difference in dimensions.

The present invention is not limited to the above described preferred embodiment thereof; the rights sought are defined by the following claims, within the scope of which many modifications can be envisaged.

What is claimed is:

1. A method for determining the hardness of a vegetable or fruit, comprising the steps of:.
   (a) causing an impactor element to be brought into contact with the fruit or the vegetable a plurality of times; and
   (b) measuring the impact of the impactor element each time it is brought into contact with the fruit or vegetable in order to determine the hardness of the fruit or vegetable over at least a portion of the surface thereof.

2. The method as claimed in claim 1, wherein the impact is determined using a piezo-electric transducer.

3. The method as claimed in claim 1, wherein the fruit or vegetable is transported over a conveyor and wherein the impactor element co-displaces with the fruit or vegetable.

4. The method of claim 1 which further comprises the step of rotating the vegetable or fruit.

5. A device for determining the hardness of a vegetable or fruit, comprising:
   (a) a supply conveyor for supplying the vegetables or fruits,
   (b) at least one hardness measuring member for measuring the hardness of the vegetables or fruits during rotation thereof, wherein said at least one hardness measuring member is arranged above the supply conveyor; and
   (c) means for causing said at least one hardness measuring member to be brought into contact with the fruit or the vegetable a plurality of times.

6. The device as claimed in claim 5, wherein a plurality of hardness measuring members are arranged successively and are coupled to drive means for driving thereof at substantially the same speed as the supply conveyor.

7. The device as claimed in claim 6, wherein successive hardness measuring members are arranged pivotally relative to each other.

8. The device as claimed in claim 5, wherein the hardness measuring member comprises a spring member and/or damping member.

9. The device as claimed in claim 5, wherein the hardness measuring member comprises an endless tooth path or curve discs.

10. The device as claimed in claim 5, wherein the hardness measuring member comprises a spring member and/or damping member.

11. The device as claimed in claim 5, wherein the hardness measuring member comprises an endless tooth path.

12. The device as claimed in claim 5, wherein the hardness measuring member comprises curve discs.

13. The device of claim 5 which further comprises rotation means for causing the vegetables or fruits to rotate on the supply conveyor.

14. A method for determining a property of a vegetable or fruit, comprising the steps of:
   (a) causing a transducer to be brought in the vicinity of the fruit or the vegetable a plurality of times; and
   (b) measuring a property of the fruit or vegetable in order to determine the property of a vegetable or fruit over at least a portion of the surface thereof.

15. The method of claim 14 which further comprises the step of rotating the vegetable or fruit.

16. A device for determining a property of a vegetable or fruit, comprising:
   (a) a supply conveyor for supplying the vegetables or fruits;
   (b) at least one sensor member for measuring a property of the vegetables or fruits during rotation thereof; and
   (c) means for causing said at least one sensor member to be brought into contact with the fruit or the vegetable a plurality of times.

17. The device as claimed in claim 16, wherein the supply conveyor is provided with brush rollers with slip-resistant means.

18. The device of claim 16 which further comprises rotation means for causing the vegetables or fruits to rotate on the supply conveyor.

19. The device as claimed in claim 16, wherein said at least one sensor member is arranged adjacent to one or more wheels.

20. The device as claimed in claim 16, wherein the supply conveyor is provided with brush rollers with slip-resistant means.

21. A device for determining a property of a vegetable or fruit, comprising:
   (a) a supply conveyor for supplying the vegetables or fruits;
   (b) rotation means for causing the vegetables or fruits to rotate on the supply conveyor; and
   (c) at least one sensor member for measuring a property of the vegetables or fruits during rotation thereof; and (d) means for causing said at least one sensor member to be brought into contact with the fruit or the vegetable a plurality of times.

22. A device for determining a property of a vegetable or fruit, comprising:
   (a) a supply conveyor for supplying the vegetables or fruits;
   (b) at least one sensor member for measuring a property of the vegetables or fruits during rotation thereof;
   (c) drive means for driving said at least one sensor member at substantially the same speed as the supply conveyor; and
   (d) means for causing said at least one sensor member to be brought into contact with the fruit or the vegetable a plurality of times.

* * * * *